United States Patent
Jones et al.

[11] Patent Number: 6,030,221
[45] Date of Patent: Feb. 29, 2000

[54] ULTRASONIC APPARATUS AND FOR PRECISELY LOCATING CAVITATIONS WITHIN JAWBONES AND THE LIKE

[75] Inventors: Robert J. Jones, Aurora, Colo.; James H. Gordon, Fairfax, Va.

[73] Assignee: Cavitat, Inc.

[21] Appl. No.: 09/021,951

[22] Filed: Feb. 11, 1998

[51] Int. Cl.[7] .............................. A61C 5/00; A61B 8/00
[52] U.S. Cl. ............... 433/215; 128/660.02; 128/660.01
[58] Field of Search ...................... 433/215; 128/660.02, 128/660.01; 601/2

[56] References Cited

U.S. PATENT DOCUMENTS

| | | |
|---|---|---|
| 3,094,115 | 6/1963 | Polin . |
| 3,883,954 | 5/1975 | Simmering et al. . |
| 4,485,823 | 12/1984 | Yamaguchi et al. . |
| 4,499,906 | 2/1985 | Wohlgemuth et al. . |
| 4,610,255 | 9/1986 | Shimura et al. . |
| 4,673,352 | 6/1987 | Hansen . |
| 5,006,984 | 4/1991 | Steele . |
| 5,100,318 | 3/1992 | Demyun et al. . |
| 5,115,813 | 5/1992 | Ylander et al. . |
| 5,295,833 | 3/1994 | Chihiro et al. . |
| 5,358,466 | 10/1994 | Aida et al. ................................. 601/4 |
| 5,402,781 | 4/1995 | Dimarogonas . |
| 5,518,008 | 5/1996 | Cucchiaro et al. . |
| 5,564,423 | 10/1996 | Mele et al. . |
| 5,651,363 | 7/1997 | Kaufman et al. . |

OTHER PUBLICATIONS

Routine Dental Extractions Routinely Produce Cavitations, Levy et al., Journal of Advancement in Medicine, vol. 9, No. 4, Winter 1996, pp. 235–249.

More Cures for Cancer, Issels, Helfer Publishing E. Schwabe (translation from German), 24 pages.

Role of Ultrasound in Assessment of Osteoporosis, (http://www.mccueplc.com/ultrasnd.htm), 6 pages.

*Primary Examiner*—Nicholas D. Lucchesi
*Attorney, Agent, or Firm*—Evenson, McKeown, Edwards & Lenahan P.L.L.C.

[57] ABSTRACT

A method and apparatus detects cavitation in the jawbone of human. The apparatus generates an ultrasonic pulse and passes the pulse through the jawbone of a human. The pulse is detected by an ultrasonic receiving unit. Attenuations in the amplitude of the pulse are detected and displayed on a color monitor. The color monitor allows the detection of cavitations by interpreting color codes in a 4×4 matrix displayed on the monitor.

19 Claims, 1 Drawing Sheet

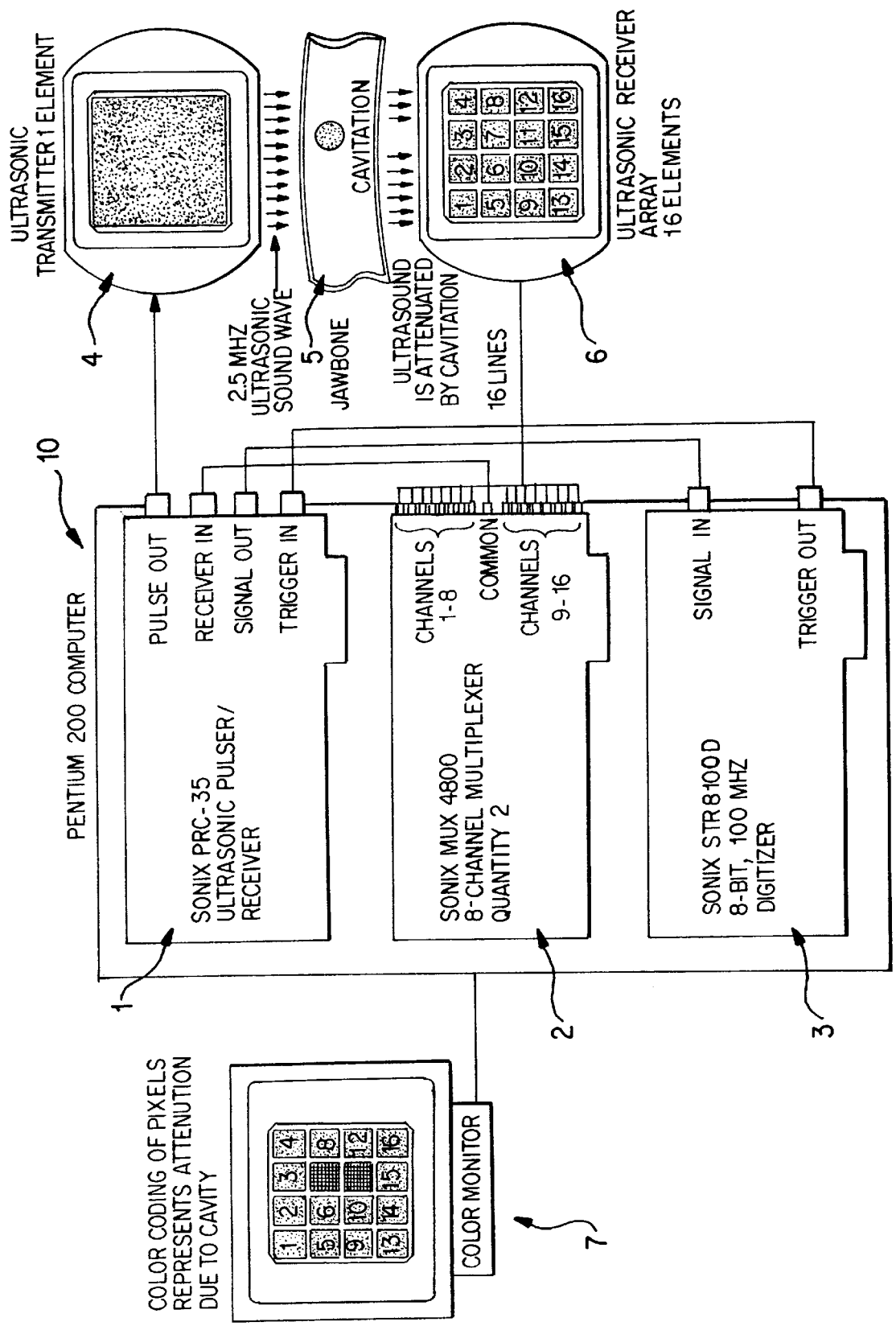

ULTRASONIC APPARATUS AND FOR PRECISELY LOCATING CAVITATIONS WITHIN JAWBONES AND THE LIKE

BACKGROUND AND SUMMARY OF THE INVENTION

The present invention relates to an apparatus and a method for locating cavitations and the like in the jawbone of a living being. More particularly, the present invention relates to an apparatus which comprises an ultrasonic transmitter and an ultrasonic receiver oppositely arranged around the jawbone of a patient to implement a method which introduces ultrasonic sound waves and determines the attenuation thereof. Thereby, a precise location and size of cavitations can be determined.

Ultrasound has long been used for a variety of applications including use in the medical field. Its predominant use has been to obtain two-dimensional soft tissue images, e.g. in a developing fetus or in a kidney. U.S. Pat. No. 5,402,781 describes a technique for measuring bone density and diagnosing osteoporosis using a frequency generator and a power amplifier to drive a transducer for inducing continuous vibration in hard tissue. Other bone and tissue analyzers are described in U.S. Pat. Nos. 4,610,255; 5,006,984; 5,518,0008; and 5,651,363.

In contrast to other techniques, ultrasound does not subject a patient to radiation. Also, it is less costly and the equipment is typically smaller in size and easier to use than X-ray equipment and the like.

More recently, ultrasound has been used to characterize the physical properties of cancellous bones using velocity of sound and broadband ultrasonic attenuation parameters which relate to elasticity, density and structure of bones. The attenuation of ultrasound in bone is derived by comparing signal amplitudes transmitted through cancellous bone with that of the same signal transmitted through water. In this connection, see *Role of Ultrasound in Assessment of Osteoporosis* (http.//www.mccueplc.com/ultrasnd.htm).

Some recent medical studies suggest that there are significant health risks associated with jawbone infections resulting from cavities in the jawbone (hereinafter, cavitations). There is an emerging view of a relationship between chronic medical diseases and jawbone infections, e.g., emaciation, rheumatic diseases, heart and other circulatory problems. See, for example, Levy and Huggins, *Routine Dental Extractions Routinely Produce Cavitations*, Journal of Advancement in Medicine, pp. 235–249 (Vol. 9, No. 4, Winter 1996), George E. Meining D.D.D., F.A.C.D., *Root Canal Cover-Up*, 1996.

We have recognized that a considerable advantage to patient wellbeing can be gained by the ability to accurately detect the location of such cavitations within the jawbone of a human patient and that ultrasound technology is the most effective way to provide this ability.

The use of ultrasound technology in the dental field is known and has generally been limited to root canal treatment. During a root canal procedure, removing infected nerve endings and filling with an inert substance are required. Before the tooth under treatment is filled with a sterile substance, the canals of the teeth containing the infected nerve endings require cleaning to ensure that the entire nerve ending is removed and thus to prevent later reinfection. During this nerve removal and cleaning, the depths of the canals are increased. To aid in this procedure, prior art techniques disclose the use of ultrasound to either detect the depth of root canals, or to diagnose the health of teeth tissue (i.e., teeth pulp).

Another use for ultrasound technology in the dental field has been in the diagnosis of periodontal pockets. Periodontists can use metal probes to determine the depths of periodontal pockets during inspections for gum disease. The prior art teaches the use of ultrasound to determine the depths of periodontal pockets, with deeper pockets indicating the likelihood of gum disease. Thus, the need for the invasive probing associated with the prior art methods of measuring dental pockets would be eliminated.

One known method and apparatus for performing ultrasound measurements is described in U.S. Pat. No. 5,100,318. The presence of diseased gum tissue by measuring the depth of the periodontal pocket along an outer surface of a tooth. In particular, a first ultrasonic pulse travel path having a fixed, reflected delay time and a second ultrasound pulse travel path having a variable, reflected delay time are established. The difference between the fixed, reflected time delay time of the first ultrasonic pulse echo pulse reflected at the gum line and the variable, reflected delay time of a second ultrasonic echo pulse reflected from the bone surface at the bottom of the periodontal pocket is measured. The difference between these reflected delay times is displayed and indicates the depth measurement for the periodontal pocket.

U.S. Pat. No. 5,115,813 describes an ultrasound based measurement method and apparatus for examining dental tissue, in particular teeth. The method involves the use of ultrasound to determine the health of teeth by subjecting them to a low frequency vibration and determining the intensity and delay of returning echo signals in relation to the pulse transmitted to the teeth under examination. The intensity and delay of the echo signals is used to form a picture which dentists can use to determine the overall health of dental tissue (i.e., teeth pulp, root paths, etc.).

Dental root canal diagnosis and treatment are the subjects of U.S. Pat. No. 5,295,833. During a root canal procedure, a dentist uses a probing tool to clean the roots of an infected tooth. Usually the root is enlarged to ensure the complete removal of the nerve from the canal path. This procedure is generally performed based on the experience of the dentist and is, more or less, completed using trial and error. Dental diagnosing and treating equipment is proposed in this patent document to enable a dentist to determine the exact depth of root canals during such root canal procedures. Ultrasound is used in this known approach to detect the depth of the canal, thus improving the less precise conventional root canal cleaning procedure.

U.S. Pat. No. 4,485,823 also proposes a dental diagnostic apparatus using ultrasound. That is, the apparatus is intended to measure environmental tissue of the teeth and numerically identify the degree of health. To effect this measurement, the apparatus is provided with an oscillation converter for converting electrical oscillation into mechanical oscillation. A probe is connected to the converter and is brought into contact with a patient's tooth for applying the mechanical oscillation thereto. The patient has a means for actuation when he or she detects the sense threshold of the oscillation applied through the probe. This approach is intended to allow the dentist to more specifically diagnose the health of the tissue without visual examination.

Similarly, U.S. Pat. No. 3,883,954 discloses the use of acoustic vibrations produced by dental occlusions for providing a viewable display. U.S. Pat. No. 3,094,115 proposes to provide a tooth mobility measuring instrument using a piezoelectric transducer in a small probe intended for ready insertion into an oral cavity. A percussion instrument is described in U.S. Pat. No. 4,499,906 whereby the degree of looseness of teeth is determined. Finally, U.S. Pat. No. 4,673,352 shows a device which uses transmit times of an ultrasonic pulse to measure relative jaw positions and movements.

Whereas the use of ultrasound has in the past been limited to soft tissue imaging, bone analysis and treatment of disorders of the teeth (i.e., root canals and gum disease), it is an object of the present invention to provide an apparatus and novel method using ultrasound for detecting with great accuracy cavitations within a person's jawbone, not the teeth themselves, thereby permitting medical personnel to undertake corrective action and prevent further complications or harmful side effects.

The foregoing object has been achieved in accordance with the present invention by generating an output pulse with an ultrasonic pulser/receiver and by configuring a multiplexer in order to output a single output to a common output from a plurality of sequentially selected input channels. An ultrasonic sound wave passed through the jawbone of a patient is subsequently received by a multiple-element (e.g., 16 elements) ultrasonic receiver array coupled to the multiplexer and converted into an electrical signal. An ultrasonic sound wave is generated using a single element ultrasonic transmitter or the like coupled to the ultrasonic pulser/receiver based on the digital output pulse generated by the ultrasonic pulser/receiver. A digital output trigger is produced and the electrical signal is converted into a digital value using a digitizer.

Cavitations within the jawbone of a patient are therefore located quickly, easily and precisely by displaying on the monitor the digital value produced from the signals of each of the array elements representing the attenuation of a sound wave generated by the ultrasonic transmitter element that is passed through the jawbone. Thus, the medical profession now has the ability to more easily treat cavitations which increasingly are believed to cause health problems.

BRIEF DESCRIPTION OF THE DRAWING

Other objects, advantages and novel features of the present invention will become apparent from the following detailed description of the invention when considered in conjunction with the accompanying drawing wherein the sole FIGURE is a schematic diagram of the novel cavitation detecting arrangement which, in relation to the jawbone of a patient, precisely detects cavitations in accordance with the method of the present invention.

DETAILED DESCRIPTION OF THE DRAWING

The sole FIGURE shows a portion of the jawbone 5 of a patient in which the presence and the location of cavitation represented by the solid dark circle is detected by emitting an ultrasonic sound wave via a one-element ultrasonic pulse transmitted by an ultrasonic pulser/receiver 1. The ultrasonic pulser/receiver 1 of the type used to implement the invention is well know in the art and can be, for example, a commercially available one such as a SONIX PRC-35 manufactured by Sonix, Inc. of Springfield, Va. The location or inclusion of a cavitation within the jawbone 5 has the effect of attenuating the amplitude of the sound wave (shown by the parallel lines above the jawbone 5) as it passes though the jawbone 5.

A sixteen channel multiplexer (in practice, a unit comprising two 8-channel multiplexers, such as a Sonix model MUX 4800), is connected with the ultrasonic pulser/receiver 1 and a digitizer 3 such as a commercially available SONIX STR8 100D, 8-bit, 100 MX digitizer also produced by Sonix, Inc. Multiple channels of the multiplexer 2 are sequentially selected. The one-element ultrasonic transmitter element 4 is excited by the pulser/receiver 1 when the latter is triggered by the digitizer 3 to produce an ultrasonic sound wave having a frequency of, for example, about 2.5 MHz. The ultrasonic sound wave is passed through the patient's jawbone 5 to detect and precisely locate the presence of one or more cavitations within the jawbone 5 by virtue of the attenuation of the strength of the wave amplitude.

In order to precisely determine and depict the exact location of the cavitations, a 16-element ultrasonic receiver array 6 is connected to the bus of the multiplexer 2 to detect the sound wave whose amplitude is proportional to the attenuation through the jawbone 5. The ultrasonic receiver array 6 is positioned on the side of the patient's jawbone 5 opposite to the transmitter 4 and comprises an array of multiple transducer elements corresponding to the channels of the multiplexer 2, e.g. sixteen in the illustrated embodiment. It will, of course, be understood that the number of channels and array elements can be varied without departing from the scope of the present invention.

The sound wave is converted into an electrical signal by the ultrasonic pulser/receiver array 6 and sent to the multiplexer 2. The multiplexer 2 sequentially routes one of a plurality of inputs to a "COMMON" output.

This common output is fed to the digitizer 3, where the electrical signal is converted into an 8-bit digital value that represents 256 levels. A processor, e.g. a "Pentium"® 200, located within a computer 10 processes the 8-bit digital data and displays, on a color monitor 7, a 4 ×4 color coded image representing the attenuation of the sound wave through the patient's jawbone 5. This attenuation represents the presence and precise location of a cavitation within the jawbone 5. Of course, the results can also be printed out, remotely displayed at another location and/or stored for subsequent retrieval.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An apparatus for detecting bone cavitations, comprising:

an ultrasonic pulser/receiver for generating an output pulse;

an ultrasonic transmitter coupled to the ultrasonic pulser/receiver for generating an ultrasonic sound wave based on the output pulse generated by the ultrasonic pulser/receiver;

a multiplexer operatively coupled to the pulser/receiver and configured to output a single output signal to a common output thereof from a plurality of input channels therein;

an ultrasonic receiver array operatively coupled to the multiplexer for receiving an attenuated ultrasonic sound wave passed through the bone and converting the same into an electrical signal supplied to the input channels of the multiplexer;

a digitizer for receiving a single output signal and converting the same into a digital value representing a predetermined number of levels;

a processor for building up a color coded image from the data obtained from each channel representative of an extent of attenuations of the sound wave through the bone; and a device for displaying the color coded image.

2. An apparatus according to claim 1, wherein the ultrasonic array has a plurality of receiving elements.

3. An apparatus according to claim 1, wherein the frequency of the output pulse in the range of about 2.5 MHz.

4. An apparatus according to claim 3, wherein the frequency of the sound wave based on the output pulse is about 2.5 MHz.

5. An apparatus according to claim 3, wherein the digital output trigger has a frequency of about 100 MHz.

6. An apparatus according to claim 1, wherein the digital value is comprised of 8-bits representing 256 levels of data.

7. An apparatus according to claim 1, wherein the displaying device is a monitor for visual display.

8. A method for detecting a bone cavitation, comprising the steps of locating an ultrasonic receiver array adjacent one side of a bone region to be examined;

locating an ultrasonic transmitter adjacent a side of the bone region opposite the receiver array;

sequentially selecting data from the receiver array;

generating and supplying a pulse signal to the transmitter so as to cause emission of an ultrasonic wave directed toward the bone region and toward the receiver array adjacent the opposite side of the bone region;

converting an attenuated sound wave received at sequentially selected portions of the receiver array into an input signal to form a succession of input signals; and processing the input signals to obtain color-coded data representative of sound attenuation measuring the extent and location of the bone cavitation.

9. A method according to claim 8, wherein the bone region is a jawbone of a human being.

10. A method according to claim 8, wherein the generated pulse signal has a frequency is in the range of about 2.5 MHz.

11. A method according to claim 10, wherein the emitted sound wave from the transmitter has a frequency of about 2.5 MHz.

12. A method according to claim 8, wherein the processing step includes digitizing a common output signal based on the succession of input signals.

13. A method according to claim 12, wherein the digitizing step assigns a digital value to data from respective channels corresponding to the instantaneously selected portions of the receiver array.

14. A method according to claim 13, wherein the digital value is comprised of 8-bits representing 256 data levels.

15. A method according to claim 12, wherein the digitizing step is performed by a digitizer having an operating frequency of about 100 MHz.

16. A method according to claim 8, wherein the processing step includes the step of visually displaying the processed color-coded data.

17. A method according to claim 16, wherein the displayed color coded data is in the form of a 4×4 image.

18. A method according to claim 8, wherein the ultrasonic receiver array comprises multiple elements corresponding to the sequentially selected portions.

19. A method according to claim 8, wherein the ultrasonic transmitter is a single-element type.

* * * * *